US012692227B2

(12) United States Patent
Okazoe et al.

(10) Patent No.: US 12,692,227 B2
(45) Date of Patent: Jul. 28, 2026

(54) METHOD FOR PRODUCING ARYL THIOL ESTER COMPOUND

(71) Applicants: AGC Inc., Tokyo (JP); The University of Tokyo, Tokyo (JP)

(72) Inventors: Takashi Okazoe, Tokyo (JP); Tim Gatzenmeier, Tokyo (JP); Kyoko Nozaki, Tokyo (JP)

(73) Assignees: AGC Inc., Tokyo (JP); The University of Tokyo, Tokyo (JP)

( * ) Notice: Subject to any disclaimer, the term of this patent is extended or adjusted under 35 U.S.C. 154(b) by 512 days.

(21) Appl. No.: 18/240,613

(22) Filed: Aug. 31, 2023

(65) Prior Publication Data

US 2023/0406819 A1 Dec. 21, 2023

Related U.S. Application Data

(63) Continuation of application No. PCT/JP2022/008983, filed on Mar. 2, 2022.

(30) Foreign Application Priority Data

Mar. 2, 2021 (JP) ................................ 2021-032819

(51) Int. Cl.
*C07C 327/16* (2006.01)
*B01J 23/72* (2006.01)
*B01J 31/02* (2006.01)

(52) U.S. Cl.
CPC ............ *C07C 327/16* (2013.01); *B01J 23/72* (2013.01); *B01J 31/0244* (2013.01)

(58) Field of Classification Search
None
See application file for complete search history.

(56) References Cited

PUBLICATIONS

Petrillo et al., "The Reactivity of Sulfur Nucleophiles Towards Arenediazonium Tetrafluoroborates in Aprotic Solvents: Synthesis of S-Aryl Thioacetates" Tetrahedron Letters, 1988, vol. 29(33), p. 4185-4188 (4 pages).
Petrillo et al., "The Reaction Between Arenediazonium Tetrafluoroborates and Alkaline Thiocarboxylates in DMSO: A Convenient Access to Aryl Thiolesters and Other Aromatic Sulfur Derivatives" Tetrahedron, 1989, vol. 45(23), p. 7411-7420 (10 pages).
Rossi et al., "Aromatic Substitution by the $S_{RN}1$ Reaction", Organic Reactions, vol. 54, 1999, p. 30-33, Nucleophiles from Sulfur (p. 30-33) (5 pages).
Matheis et al., "Sandmeyer-Type Trifluoromethylthiolation and Trifluoromethylselenolation of (Hetero)Aromatic Amines Catalyzed by Copper" Chemistry A European Journal, 2016, 22, p. 79-82 (4 pages).
Vera et al., "Thiofunctionalization of Electron-Rich Heteroarenes through Magnesiation and Trapping with Octasulfur" Advanced Synthesis Catalysis, 2021, 363, p. 5099-5105 (7 pages).
Kovacs et al., "Practical Reagents and Methods for Nucleophilic and Electrophilic Phosphorothiolations" Advanced Synthesis Catalysis, 2018, 360, p. 1913-1918 (6 pages).
Zhang et al., "Perfluorocarbon-based nanomedicine: emerging strategy for diagnosis and treatment of diseases" MRS Communications, 2018, vol. 8, p. 303-313 (11 pages).
Cai et al., "Bioreducible Fluorinated Peptide Dendrimers Capable of Circumventing Various Physiological Barriers for Highly Efficient and Safe Gene Delivery" ACS Applied Materials and Interfaces, 2016, vol. 8, p. 5821-5832 (12 pages).
Godeau et al., "Fluorocarbon oligonucleotide conjugates for nucleic acids delivery" Medicinal Chemistry Communications, 2010, vol. 1. p. 76-78 (3 pages).
Ellipilli et al., "Perfluoroalkylchain conjugation as a new tactic for enhancing cell permeability of peptide nucleic acids (PNAs) via reducing the nanoparticle size" Chemical Communications, 2016, vol. 52, p. 521-524 (4 pages).
Rochambeau et al., ""DNA—Teflon" sequence-controlled polymers" Polymer Chemistry, 2016, vol. 7, p. 4998-5003 (7 pages).
Metelev et al., "Fluorocarbons Enhance Intracellular Delivery of Short STAT3-sensors and Enable Specific Imaging" Theranostics, 2017, vol. 7, p. 3354-3368 (15 pages).
Murayama et al., "Highly Stable Duplex Formation by Artificial Nucleic Acids Acyclic Threoninol Nucleic Acid (aTNA) and Serinol Nucleic Acid (SNA) with Acyclic Scaffolds" Chemistry A European Journal, 2013, vol. 19, p. 14151-14158 (8 pages).
(Continued)

*Primary Examiner* — Valerie Rodriguez-Garcia
(74) *Attorney, Agent, or Firm* — Oblon, McClelland, Maier & Neustadt, L.L.P.

(57) ABSTRACT

The present invention provides a production method capable of synthesizing an aryl thiol ester compound under mild conditions rapidly at a high yield. The present invention provides a method for producing an aryl thiol ester compound including producing an aryl thiol ester compound represented by the following general formula (1) from a diazonium compound represented by the following general formula (2) and a thioate compound represented by the following general formula (3) by a Sandmeyer-type coupling reaction using a catalyst, [wherein $A^1$ and $A^2$ are each independently an optionally substituted aryl group or an optionally substituted heteroaryl group; $X^1$ is a monovalent anion; and $M^1$ is a monovalent cation].

[Chemical Formula 1]

(2)

(3)

(1)

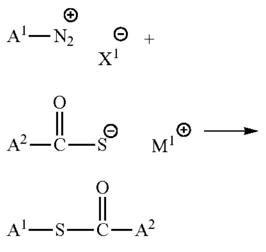

3 Claims, No Drawings

(56) References Cited

PUBLICATIONS

Watanabe et al., "Synthesis of fluorine containing oligonucleotides for cell membrane permeability and their assay", A25-2am-09, The chemical society of Japan, Lecture preprints of the 101st CSJ Annual Meeting (2021), 2021 (1 page) (with English Abstract).
Sheppard, "Communications to the Editor" 1960, vol. 82, p. 4751-4752 (2 pages).
Ou et al., "Oxidative fluorination of S, Se and Te compounds" Journal of Fluorine Chemistry, 2000, vol. 101, p. 279-283 (5 pages).
Moriarty et al., "Oxidation of Carbonyl Compounds with Organohypervalent lodine Reagents" Organic Reactions, vol. 54, 1999 (130 pages).

METHOD FOR PRODUCING ARYL THIOL ESTER COMPOUND

This application is a continuation application of International Application No. PCT/JP2022/008983, filed on Mar. 2, 2022, which claims the benefit of priority of the prior Japanese Patent Application No. 2021-032819, filed on Mar. 2, 2021 in Japan, the content of which are incorporated herein by reference.

TECHNICAL FIELD

The present invention relates to a method for producing an aryl thiol ester compound.

BACKGROUND ART

Aryl thiol ester compounds have a highly electrophilic carbonyl group and can be used as electrophilic reagents in acyl transfer processes and carbanion precursors in condensation reactions. Aryl thiol ester compounds are useful as intermediates in synthesizing organic compounds that are raw materials for organic materials, biochemical products, pharmaceuticals, etc. Therefore, the development of more efficient production methods is required.

An aryl thiol ester compound can be synthesized, for example, using a nucleophilic reaction of a thiolate with a carboxylic acid derivative. For compounds that are difficult to synthesize by this method, it is necessary to try another synthetic methods. For example, there is a synthetic method utilizing the thermal rearrangement of O-arylthioesters and a method of reacting an electrophilic substrate such as a diaryliodonium salt or an aryl halide with an organometallic catalyst. However, since these methods require harsh reaction conditions, a method capable of synthesizing under mild conditions is desired. As a method for synthesizing under milder conditions, for example, it has been reported that various S-arylthioacetates can be synthesized with yields of 40 to 60% by treating aryldiazonium tetrafluoroborate with potassium thioacetate in DMSO at room temperature (Non-Patent Document 1, Non-Patent Document 2).

CITATION LIST

Non-Patent Document

[Non-Patent Document 1] Petrillo et al., Tetrahedron Letters, 1988, vol. 29(33), p. 4185-4188.
[Non-Patent Document 2] Petrillo et al., Tetrahedron, 1989, vol. 45(23), p. 7411-7420.

SUMMARY OF INVENTION

Technical Problems

An object of the present invention is to provide a production method capable of synthesizing an aryl thiol ester compound under mild conditions rapidly at a high yield.

Solution to Problem

The present inventors have found that when synthesizing an aryl thiol ester compound by using a Sandmeyer-type coupling reaction, it is possible to rapidly synthesize a thioate compound from a diazonium compound under mild conditions, and further, found that the yield can be improved by using a catalyst, and thus completed the present invention.

That is, the present invention is as follows.

[1] A method for producing an aryl thiol ester compound, comprising producing an aryl thiol ester compound represented by the following general formula (1) from a diazonium compound represented by the following general formula (2) and a thioate compound represented by the following general formula (3) by a Sandmeyer-type coupling reaction using a catalyst.

[Chemical Formula 1]

$$A^1—N_2^{\oplus}\ X^{1\ominus} \qquad (2)$$

[In the formula, $A^1$ is an optionally substituted aryl group or an optionally substituted heteroaryl group; $X^1$ is a monovalent anion.]

[Chemical Formula 2]

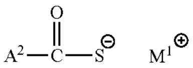

(3)

[In the formula, $A^2$ is an optionally substituted aryl group or an optionally substituted heteroaryl group; $M^1$ is a monovalent cation.]

[Chemical Formula 3]

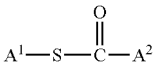

(1)

[In the formula, $A^1$ and $A^2$ are the same as described above.]

[2] The method for producing an aryl thiol ester compound according to [1], wherein the catalyst is a transition metal complex.

[3] The method for producing an aryl thiol ester compound according to [2], wherein the transition metal complex is a copper complex.

[4] The method for producing an aryl thiol ester compound according to [2] or [3], wherein the transition metal complex includes a bidentate nitrogen chelate ligand.

[5] The method for producing an aryl thiol ester compound according to any one of [2] to [4], wherein the transition metal complex is composed of a copper (1) ion and one or more ligands selected from the group consisting of 1,10-phenanthroline, 2,2'-bipyridine and derivatives thereof.

[6] The method for producing an aryl thiol ester compound according to any one of [1] to [5], wherein prior to the Sandmeyer-type coupling reaction, an aminoaryl compound represented by the following general formula (4) is diazotized to produce the compound represented by the general formula (2).

Chemical Formula 4

$$A^1\text{-}NH_2 \qquad (4)$$

[In the formula, $A^1$ is the same as described above.]

Advantageous Effects of Invention

According to the method of the present invention, an aryl thiol ester compound can be efficiently synthesized with a high yield.

Description of Embodiments

In the present invention and the specification of the present application, "$C_{p1-p2}$" (p1 and p2 are positive integers satisfying p1<p2) means a group having p1 to p2 carbon atoms.

In the present invention and the specification of the present application, a "$C_{1-6}$ alkyl group" is an alkyl group having 1 to 6 carbon atoms, and may be linear or branched. Examples of the $C_{1-6}$ alkyl group include a methyl group, an ethyl group, an n-propyl group, an isopropyl group, an n-butyl group, an isobutyl group, a sec-butyl group, a tert-butyl group, an n-pentyl group, an isopentyl group, an neopentyl group, tert-pentyl group, n-hexyl group and the like.

In the present invention and the specification of the present application, the term "$C_{1-6}$ alkoxy group" refers to a group in which an oxygen atom is bonded to the terminal end of a $C_{1-6}$ alkyl group. A $C_{1-6}$ alkoxy group may be linear or branched. Examples of the $C_{1-6}$ alkoxy group include a methoxy group, an ethoxy group, a propoxy group, an isopropoxy group, a butoxy group, a tent-butoxy group, a pentyloxy group, a hexyloxy group and the like.

In the present invention and the specification of the present application, the term "$C_{2-6}$ alkenyl group" refers to a group in which at least one carbon-carbon bond of an alkyl group having 2 to 6 carbon atoms is an unsaturated bond. The $C_{2-6}$ alkenyl group may be linear or branched. Examples of the $C_{2-6}$ alkenyl group include a vinyl group, an allyl group, a butenyl group, a pentenyl group, a hexenyl group and the like.

In the present invention and the specification of the present application, the term "$C_{2-7}$ acyl group" refers to a group in which the hydrocarbon group moiety obtained by removing the carbonyl group from the acyl group is a $C_{1-6}$ alkyl group, a $C_{2-6}$ alkenyl group, a 5- to 6-membered aryl group or a 5- to 6-membered heteroaryl group. The hydrocarbon group moiety of the acyl group may be linear or branched. Examples of the $C_{2-7}$ acyl group include a formyl group, an acetyl group, a propanoyl group, a propenoyl group, a benzoyl group and the like.

In the present invention and the specification of this application, the term "halogen atom" refers to a fluorine atom, a chlorine atom, a bromine atom, or an iodine atom. The term "halogen atom other than a fluorine atom" refers to a chlorine atom, a bromine atom, or an iodine atom. As the "halogen atom other than a fluorine atom", a chlorine atom or a bromine atom is preferable, and a chlorine atom is particularly preferable.

Moreover, hereinafter, the term "compound (n)" refers a compound represented by formula (n).

The method for producing an aryl thiol ester compound according to the present invention is a method for producing an aryl thiol ester compound represented by the following general formula (1) (hereinafter, may be referred to as "aryl thiol ester compound (1)") from a diazonium compound represented by the following general formula (2) (hereinafter, may be referred to as "diazonium compound (2)") and a thioate compound represented by the following general formula (3) (hereinafter, may be referred to as "thioate compound (3)"), by a Sandmeyer-type coupling reaction. Sandmeyer-type coupling reactions are nucleophilic aromatic substitution reactions by a radical mechanism. Aryl thiol ester compound (1) can be rapidly produced under relatively mild conditions of 0 to 40° C. by using a Sandmeyer-type coupling reaction.

[Chemical Formula 5]

(2)

(3)

(1)

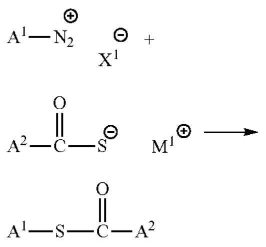

In the general formula (1), general formula (2) and general formula (3), $A^1$ and $A^2$ are each independently an optionally substituted aryl group or an optionally substituted heteroaryl group. The aryl group is not particularly limited, and examples thereof include a phenyl group, a naphthyl group, an anthryl group, a 9-fluorenyl group and the like, and a phenyl group is particularly preferable. The heteroaryl group is not particularly limited, and examples thereof include a pyridyl group, a pyrazinyl group, a pyrimidinyl group, a pyridazinyl group, a pyrazolyl group, a quinolyl group, an isoquinolyl group, a pyrrolyl group, a imidazolyl group, a indolyl group, a furyl group, a benzofuryl group, a thienyl group, a benzothienyl group, an oxazolyl group, an isoxazolyl group, a thiazolyl group, an isothiazolyl group and the like.

The term "optionally substituted aryl group" refers to a group in which one or more, preferably 1 to 3, hydrogen atoms bonded to the carbon atoms of the aryl group are substituted with other functional groups. Similarly, the term "optionally substituted heteroaryl group" refers to a group in which one or more, preferably 1 to 3 hydrogen atoms bonded to the carbon atoms of the heteroaryl group are substituted with other functional groups. When there are two or more substituents, they may be the same or different.

$A^1$ and $A^2$ may have one or two or more substituents in addition to the sulfur atom to be fluorinated. Examples of the substituents include a halogen atom, an alkyl group, an alkenyl group, an alkoxy group, an aryl group, an acyl group, a hydroxy group, a carboxy group, a cyano group, an amino group, a nitro group and the like. The alkyl group is preferably a $C_{1-6}$ alkyl group, the alkenyl group is preferably a $C_{2-6}$ alkenyl group, the alkoxy group is preferably a $C_{1-6}$ alkoxy group, and the acyl group is a $C_{2-7}$ acyl group.

In general formula (2), $X^1$ is a monovalent anion. Examples of $X^1$ include $BF_4^-$, $PF_6^-$ and the like.

In general formula (3), $M^1$ is a monovalent cation. Examples of $M^1$ include a sodium ion, a potassium ion and the like.

The diazonium compound (2) is preferably a compound in which $A^1$ in the general formula (2) is an optionally substituted phenyl group or pyridyl group, and more preferably a compound in which $A^1$ is a phenyl group optionally substituted with 1 to 3 substituents selected from the group consisting of a halogen atom, an alkyl group, an alkenyl group, an alkoxy group, an aryl group, an acyl group, a hydroxy group, a carboxy group, a cyano group, an amino group and a nitro group; or a pyridyl group optionally substituted with 1 to 3 substituents selected from the group consisting of a halogen atom, an alkyl group, an alkenyl group, an alkoxy group, an aryl group, an acyl group, a hydroxy group, a carboxy group, a cyano group, an amino group and a nitro group.

The thioate compound (3) is preferably a compound in which $A^2$ in the general formula (3) is an optionally substituted phenyl group or pyridyl group, and $M^1$ is $Na^+$ or $K^+$, more preferably a compound in which $A^2$ is a phenyl group optionally substituted with 1 to 3 substituents selected from the group consisting of a halogen atom, an alkyl group, an alkenyl group, an alkoxy group, an aryl group, an acyl group, a hydroxy group, a carboxy group, a cyano group, an amino group and a nitro group; or a pyridyl group optionally substituted with 1 to 3 substituents selected from the group consisting of a halogen atom, an alkyl group, an alkenyl group, an alkoxy group, an aryl group, an acyl group, a hydroxy group, a carboxy group, a cyano group, an amino group and a nitro group, and $M^1$ is $Na^+$ or $K^+$.

By reacting the diazonium compound (2) with the thioate compound (3), an aryl thiol ester compound (1) represented by the general formula (1) (in the formula, $A^1$ and $A^2$ are each independently an optionally substituted phenyl group or an optionally substituted pyridyl group) can be synthesized.

The amount of the diazonium compound (2) and the thioate compound (3) added to the reaction system is not particularly limited as long as it is at least a stoichiometric amount. From the viewpoint of reaction efficiency and cost, the amount of the thioate compound (3) present in the reaction solution of the Sandmeyer-type coupling reaction at the start of the reaction is preferably 1 to 5 equivalents, more preferably 1 to 2 equivalents of the thioaryl compound (2).

In the present invention, the Sandmeyer-type coupling reaction for coupling the diazonium compound (2) and the thioate compound (3) is performed using a catalyst. Aryl thiol ester compound (1) can be synthesized at a high yield by a Sandmeyer-type coupling reaction using a catalyst. The catalyst to be used is not particularly limited as long as it can catalyze the Sandmeyer-type coupling reaction, and it is preferable to use a transition metal complexes as the catalyst, since the reaction can proceed efficiently in a temperature environment of 0 to 40° C.

As the transition metal that constitutes the transition metal complex, for example, copper, silver, palladium, gold, nickel or the like can be used. Further, the ligand constituting the transition metal complex is not particularly limited as long as it has a lone electron pair capable of chelating to the transition metal to be used, and it may be a monodentate ligand or a bidentate ligand or a polydentate ligand. The transition metal complex used in the present invention is preferably a copper complex, more preferably a complex composed of a copper (I) ion and a bidentate ligand, more preferably a complex composed of copper (I) ion and a bidentate nitrogen chelating ligand.

Examples of the bidentate nitrogen chelating ligand include 1,10-phenanthroline, 2,2'-bipyridine and derivatives thereof. Examples of the derivative of 1,10-phenanthroline include a compound in which one or more hydrogen atoms bonded to the carbon atoms of 1,10-phenanthroline are substituted with a halogen atom, a $C_{1-6}$ alkyl group, an aryl group, a heteroaryl group, a nitro group, an amino group, a hydroxy group, a carbonyl group, a carboxy group or the like. Similarly, examples of the derivative of 2,2'-bipyridine include a compound in which one or more hydrogen atoms bonded to the carbon atoms of 2,2'-bipyridine are substituted with a halogen atom, a $C_{1-6}$ alkyl group, an aryl group, a hetero aryl group, a nitro group, an amino group, a hydroxy group, a carbonyl group, a carboxy group or the like. Examples of the halogen atom, $C_{1-6}$ alkyl group, aryl group and the heteroaryl group are the same as those mentioned above.

Specific examples of the derivative of 1,10-phenanthroline include 2-methyl-1,10-phenanthroline (CAS No: 3002-77-5), 5-methyl-1,10-phenanthroline hydrate (CAS No: 002-78-6), 4,7-dimethyl-1,10-phenanthroline (CAS No: 3248-05-3), 5,6-dimethyl-1,10-phenanthroline (CAS No: 3002-81-1), 3,4,7,8-tetramethyl-1,10-phenanthroline (CAS No: 1660-93-1), bathophenanthroline (4,7-diphenyl-1,10-phenanthroline) (CAS No: 1662-01-7), bathocuproine (2,9-dimethyl-4,7-diphenyl-1,10-phenanthroline) (CAS No: 4733-39-5), 2-bromo-1,10-phenanthroline (CAS No: 22426-14-8), 3-bromo-1,10-phenanthroline (CAS No: 66127-01-3), 5-bromo-1,10-phenanthroline (CAS No: 40000-20-2), 2-chloro-1, 10-phenanthroline (CAS No: 7089-68-1), 4,7-dibromo-1,10-phenanthroline (CAS No: 156492-30-7), 3,8-dibromo-1,10-phenanthroline (CAS No: 100125-12-0), 2,9-dichloro-1,10-phenanthroline (CAS No: 29176-55-4), 1,10-phenanthroline-5,6-dione (CAS No: 27318-90-7), 4,7-dihydroxy-1,10-phenanthroline (CAS No: 3922-40-5), 5-nitro-1,10-phenanthroline (CAS No: 4199-88-6), 5-amino-1,10-Phenanthroline (CAS No: 54258-41-2) and the like.

Examples of the derivative of 2,2'-bipyridine include 4,4'-dimethyl-2,2'-bipyridyl (CAS No: 1134-35-6), 6,6'-dimethyl-2, 2'-bipyridyl (CAS No: 4411-80-7), 4,4'-di-tert-butyl-2,2'-bipyridyl (BBBPY) (CAS No: 72914-19-3), 4, 4'-bis(trifluoromethyl)-2,2'-bipyridyl (CAS No: 142946-79-0), 5,5'-bis(trifluoromethyl)-2,2'-bipyridyl (CAS No: 142946-80-3), 6-bromo-4,4'-dimethyl-2,2'-bipyridyl (CAS No: 850413-36-4), 5-bromo-2,2'-bipyridyl (CAS No: 15862-19-8), 4,4'-dibromo-2,2'-bipyridyl (CAS No: 18511-71-2), (CAS No: 15862-18-7), 6,6'-dibromo-2,2'-bipyridyl (CAS No: 49669-22-9), 4,4'-bis(5-hexyl-2-thienyl)-2,2'-bipyridyl (CAS No: 1047684-56-9), 4,4'-diamino-2,2'-bipyridyl (CAS No: 18511-69-8), 6,6'-diamino-2,2'-bipyridyl (CAS No: 93127-75-4), 2,2'-bipyridine-3,3'-diol (CAS No: 36145-03-6), 2,2'-bipyridine-5,5'-diol (CAS No: 2326-78-5), 2,2'-bipyridine-6,6'-diol (CAS No: 103505-54-0), 2,2'-bipyrazine (CAS No: 10199-00-5), 2,2'-biquinoline (CAS No: 119-91-5), 4,4'-dimethyl-2,2'-biquinoline (CAS No: 7654-51-5) and the like.

As the catalyst used for the Sandmeyer-type coupling reaction in the present invention, a copper complex composed of a copper (I) ion and one or more ligands selected from the group consisting of 1,10-phenanthroline, 2,2'-bipyridine and derivatives thereof is preferable, and a copper complex composed of a copper (I) ion and one or more ligands selected from the group consisting of phenanthroline, bathophenanthroline, 2,2'-bipyridine, and BBBPY is more preferable.

The amount of the catalyst added to the reaction system is not particularly limited, and may be any amount that can increase the yield of the product obtained by the Sandmeyer-type coupling reaction compared to the case where no catalyst is added. For example, the amount of the catalyst added to the reaction solution is preferably 5 to 30 mol %, more preferably 5 to 25 mol %, even more preferably 5 to 20 mol %, and even more preferably 10 to 20 mol %, with respect to the substrate diazonium compound (2). When performing the Sandmeyer-type coupling reaction, the transition metal complex may be added to the reaction solution, or a transition metal source and ligand may be added to synthesize the transition metal complex in the reaction solution. As the transition metal source, a salt of a transition metal ion constituting the desired transition metal complex and an anion ion is preferable. For example, when a copper complex composed of a copper (I) ion and a ligand is used as a catalyst, copper (I) thiocyanate (CuSCN), copper (I) bromide-dimethyl sulfide complex ($CuBr \cdot SMe_2$), copper (I) cyanide (CuCN) and the like can be mentioned as the copper (I) source.

The Sandmeyer-type coupling reaction can be carried out in a solvent inert to the reaction. Although the inert solvent is not particularly limited, an aprotic polar solvent is preferable. Examples of the aprotic polar solvent include acetonitrile (MeCN), N,N'-dimethyl formamide (DMF), N,N-diniethylacetamide, dimethylsulfoxide (DMSO), tetrahydrofuran (THF), dichloromethane (DCM), diethyl ether and the like. The solvent used for the reaction may be a mixed solvent of two or more solvents.

In the Sandmeyer-type coupling reaction, a reaction solution obtained by mixing a diazonium compound (2), a thioate compound (3), and a catalyst in a reaction solvent is allowed to react at an appropriate temperature and time. A transition metal source and a ligand may be added instead of the catalyst. The Sandmeyer-type coupling reaction proceeds under mild conditions. For example, the reaction temperature is not particularly limited as long as it is a temperature at which the reaction solvent is liquid, and it can be carried out at −40 to 130° C., preferably at −30 to 80° C., more preferably at room temperature (0 to 30° C.). For example, the Sandmeyer-type coupling reaction can be carried out at room temperature for less than 1 hour to obtain the desired aryl thiol ester compound (1) at a high yield, for example, a yield of 70% or more.

The synthesized aryl thiol ester compound (1) can be used as a substrate for synthesizing other organic compounds. For example, a pentafluorosulfanyl group-containing aryl compound can be produced by subjecting the aryl thiol ester compound (1) as a substrate to an oxidative fluorination reaction using $AgF_2$.

When the synthesized aryl thiol ester compound (1) is used as a substrate for synthesizing another organic compound, the reaction solution containing the reaction product of the Sandmeyer-type coupling reaction may be used as it is for the next reaction, or the aryl thiol ester compound (1) may be purified from the reaction solution and used in the next reaction. The purification method is not particularly limited, and a commonly used purification method such as filtration can be used.

The diazonium compound (2) used in the Sandmeyer-type coupling reaction can be produced by diazotizing an aminoaryl compound represented by the following general formula (4) (hereinafter sometimes referred to as "aminoaryl compound (4)"). In the general formula (4) below, $A^1$ is the same as the $A^1$ in the general formula (2).

Chemical Formula 6

$A^1\text{-}NH_2$ (4)

The diazotization reaction of aminoaryl compound (4) can be carried out using various diazo coupling reactions. For example, boron trifluoride and nitrite are used to synthesize a nitrosonium ion ($NO^+$) and a tetrafluoroborate ion ($BF_4^-$), which are reacted with the amino group of the aminoaryl compound (4) to form a tetrafluoroborate of the diazonium compound (2) (aryl diazonium tetrafluoroborate: $A^1\text{-}N_2^+ BF_4^-$). The diazotization reaction of the aminoaryl compound (4) can also be carried out with sodium nitrite and hydrochloric acid, in which case the hydrochloride salt of the diazonium compound (2) is produced.

The diazotization reaction can be carried out in a solvent inert to the reaction at a temperature at which the reaction solvent is liquid. As the inert solvent, the same as that as used in the Sandmeyer-type coupling reaction can be used.

When the diazonium compound (2) synthesized by the diazotization reaction of the aminoaryl compound (4) is used in the Sandmeyer-type coupling reaction, the diazotization reaction and the subsequent Sandmeyer-type coupling reaction can be carried out in one pot.

EXAMPLES

The present invention will be described below with reference to Examples, but the present invention is not limited to these Examples.

The NMR equipment used for analysis of the Examples and the Comparative Examples was JNM-EC Z 400 S (400 MHz) manufactured by JEOL Ltd. Tetramethylsilane was set at 0 PPM for $^1H$ NMR, and $C_6F_6$ was set at −162 PPM for $^{19}F$ NMR.

Example 1

4-Methoxyphenyl benzothioate was synthesized as follows.

(1) Diazotization of Aminoaryl

First, a benzenediazonium salt was synthesized by a general synthetic method.

[Chemical Formula 7]

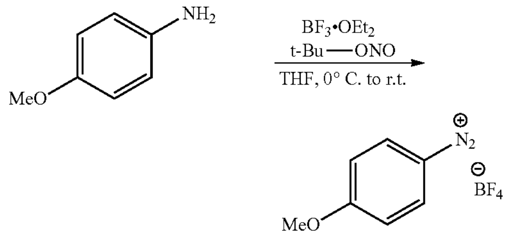

Boron trifluoride-diethyl ether complex ($BF_3 \cdot OEt_2$) (1.5 mmol, 1.5 eq.) was added to a solution of 4-methoxyaniline (1 mmol, 1 eq.) dissolved in 3 mL THF at ice-bath temperature. After stirring for 5 minutes, tert-butyl nitrite (1.2 mmol, 1.2 eq.) was added dropwise to the solution at 0° C. After stirring for an additional 15 minutes, the precipitate (benzenediazonium salt) was collected by filtration and washed with diethyl ether.

(2) Sandmeyer-Type Coupling Reaction

An aryl thiobenzoate was synthesized from benzenediazonium salt and thiobenzoate by a Sandmeyer-type coupling reaction using a copper complex catalyst. CuSCN, $CuBr \cdot SMe_2$ or $CuCN \cdot LiCl$ (THF solution) was used as the copper (I) source, and 1,10-phenanthroline (Phen), bathophenanthroline (Bathophen) or BBBPY was used as the ligand.

[Chemical Formula 8]

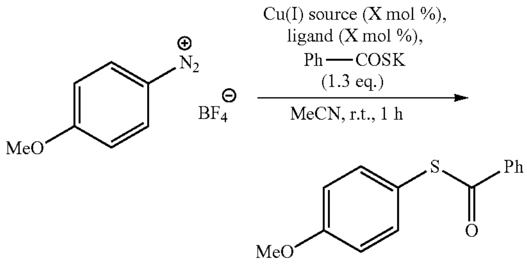

In an argon-filled drybox, a glass vial was charged with a copper (I) source (X mol %), a ligand (X mol %), potassium thiobenzoate (229 mg, 1.3 mmol) and a magnetic stir bar, followed by MeCN (1 mL), and stirred for approximately 2 minutes. The reaction mixture was a red suspension containing undissolved potassium thiobenzoate. 4-Methoxybenzenediazonium tetrafluoroborate (222 mg, 1.0 mmol) dissolved in MeCN (2 mL) was added dropwise to the reaction mixture at room temperature using a syringe. Visible nitrogen gas formation occurred during the addition. The syringe was previously washed using 1 mL of MeCN. After stirring the reaction mixture at room temperature or for 1 hour, the resulting reaction was transferred to a 50 mL flask. After adding silica to the flask, the solvent was evaporated in vacuo. Subsequently, column chromatography (hexane: DCM=2:1 to 1:1 (volume ratio)) was performed to obtain 4-methoxyphenyl benzothioate as a yellow solid.

1H NMR (400 MHz) δ8.06-8.02 (m, 2H), 7.63-7.58 (m, 1H), 7.52-7.46 (m, 2H), 7.46-7.41 (m, 2H), 7.02-6.98 (m, 2H), 3.85 (s, 3H).

Table 1 shows the copper complex catalyst (copper (1) source and ligand), the amount of copper complex used ("X mol %" in the reaction formula), the reaction temperature, and the yield (%) of 4-methoxyphenylbenzothioate in each test group. In Table 1, "/" indicates no addition. For example, for test group 9, CuSCN (12 mg, 0.1 mmol) was used as the copper (I) source, 1,10-phenanthroline (18 mg, 0.1 mmol) was used as the ligand, and 4-methoxyphenylbenzothioate (195 mg) (80% yield) was obtained.

TABLE 1

| Test Group | Copper (I) Source | Ligand | Amount of Catalyst Added (mol %) | Reaction Temperature (° C.) | Yield (%) |
|---|---|---|---|---|---|
| 1 | / | / | / | r.t. | 64.8 |
| 2 | CuSCN | / | 20 | r.t. | 62.9 |
| 3 | CuBr•SMe2 | / | 20 | r.t. | 65.3 |
| 4 | CuCN•LiCl (in THF) | / | 20 | r.t. | 65.1 |
| 5 | CuSCN | Phen | 20 | r.t. | 71.3 |
| 6 | CuSCN | Bathophen | 20 | r.t. | 75.3 |
| 7 | CuSCN | bbbpy | 20 | r.t. | 75.2 |
| 8 | CuSCN | Phen | 10 | r.t. | 80.0 |
| 9 | CuSCN | Bathophen | 10 | r.t. | 74.7 |
| 10 | CuSCN | Phen | 10 | −30° C. | 76.5 |
| 11 | CuSCN | Phen | 10 | 0° C. | 74.6 |

There was no or very little improvement in yield in test groups 2 to 4 using uncomplexed copper as a catalyst compared to test group 1 without catalyst. On the other hand, test groups 5 to 11 using a copper complex catalyst showed a clear improvement in yield regardless of the type of copper (I) source and ligand used. In particular, test group 8, in which 10 mol % of a copper complex catalyst composed of CuSCN and 1,10-phenanthroline was used with respect to benzenediazonium salt (4-methoxybenzenediazonium tetrafluoroborate), yielded an extremely high yield of 80%.

Comparing test groups 8, 10 and 11, test group 8 showed the highest yield, and test groups 10 and 11 also showed sufficient yield improvement, indicating that the effect of improving the yield by using a transition metal complex as a catalyst can be obtained even in a low-temperature environment with a reaction temperature of −30° C. to 0° C.

INDUSTRIAL APPLICABILITY

The present invention provides a method for producing an aryl thiol ester compound which can be rapidly synthesized at a high yield under relatively mild conditions. In addition, since the aryl thiol ester compound produced by the present invention is useful as an intermediate for producing various organic compounds, the present invention is useful for producing active ingredients of pharmaceuticals and agricultural chemicals, organic materials and the like.

The invention claimed is:

1. A method for producing an aryl thiol ester compound, comprising producing an aryl thiol ester compound represented by the following general formula (1) from a diazonium compound represented by the following general formula (2) and a thioate compound represented by the following general formula (3) by a Sandmeyer-type coupling reaction using a transition metal catalyst, wherein the transition metal catalyst is a copper complex and includes a bidentate nitrogen chelate ligand, (2)

$$A^1—N_2^{\oplus}\ X^{1\ominus}$$

wherein in the formula, $A^1$ is an optionally substituted aryl group or an optionally substituted heteroaryl group; $X^1$ is a monovalent anion (3)

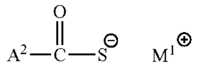

wherein in the formula, $A^2$ is an optionally substituted aryl group or an optionally substituted heteroaryl group; $M^1$ is a monovalent cation (1)

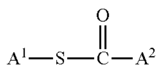

wherein in the formula, $A^1$ and $A^2$ are the same as described above.

2. The method for producing an aryl thiol ester compound according to claim 1, wherein the transition metal complex is composed of a copper (I) ion and one or more ligands selected from the group consisting of 1,10-phenanthroline, 2,2-bipyridine and derivatives thereof.

3. The method for producing an aryl thiol ester compound according to claim 1, wherein prior to the Sandmeyer-type coupling reaction, an aminoaryl compound represented by the following general formula (4) is diazotized to produce the compound represented by the general formula (2)

$$A^1\text{-}NH_2 \quad (4)$$

wherein in the formula, $A^1$ is the same as described in claim 1.

* * * * *